US008227602B2

(12) United States Patent
Gautier et al.

(10) Patent No.: US 8,227,602 B2
(45) Date of Patent: Jul. 24, 2012

(54) LABELLING OF FUSION PROTEINS WITH SYNTHETIC PROBES

(75) Inventors: Arnaud Gautier, Lausanne (CH); Kai Johnsson, Lausanne (CH); Maik Kindermann, Frankfurt (DE); Alexandre Juillerat, Paris (FR); Florent Beaufils, Rosenau (FR)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 664 days.

(21) Appl. No.: 12/309,554

(22) PCT Filed: Jul. 24, 2007

(86) PCT No.: PCT/EP2007/057597
§ 371 (c)(1),
(2), (4) Date: Jan. 22, 2009

(87) PCT Pub. No.: WO2008/012296
PCT Pub. Date: Jan. 31, 2008

(65) Prior Publication Data
US 2011/0207157 A1 Aug. 25, 2011

(30) Foreign Application Priority Data

Jul. 25, 2006 (EP) .................................... 06117779

(51) Int. Cl.
*C07D 239/02* (2006.01)
(52) U.S. Cl. ....................................................... 544/317
(58) Field of Classification Search .................. 544/317
See application file for complete search history.

(56) References Cited

U.S. PATENT DOCUMENTS 6,352,981 B1 * 3/2002 Treiber et al. ................. 514/183
2009/0186373 A1 * 7/2009 Kindermann et al. .......... 435/29

FOREIGN PATENT DOCUMENTS

| WO | WO 0107436 A2 * | 2/2001 |
| WO | 2004/031405 | 4/2004 |
| WO | WO 2004031405 A1 * | 4/2004 |
| WO | 2005/085470 | 9/2005 |
| WO | 2006/114409 | 11/2006 |

OTHER PUBLICATIONS

Ward et al., Journal of Medicinal Chemistry, 88-92 (1977).*

International Search Report issued Nov. 13, 2007 in the International (PCT) Application of which the present application is the U.S. National Stage.
M. Freccero et al., "Modeling H-Bonding and Solvent Effects in the Alkylation of Pyrimidine Bases by a Prototype Quinone Methide: A DFT Study", J. Am. Chem., Soc., vol. 125, No. 12, pp. 3544-3553, Mar. 26, 2003.
A. D. Ward et al., "Irreversible Enzyme Inhibitors. 200. Active-Site-Directed Inhibitors of Deoxycytidine Kinase", Journal of Medicinal Chemistry, vol. 20, No. 1, pp. 88-92, Jan. 1, 1977.
T.Gronemeyer et al., "Directed evolution of $O^6$-alkylguanine-DNA alkyltransferase for applications in protein labeling", Protein Engineering, Design & Selection, vol. 19, No. 7, pp. 309-316, Apr. 25, 2006.
E. M. Duguid et al., "The Structure of the Human AGT Protein Bound to DNA and its Implications for Damage Detection", J. Mol. Biol., vol. 350, No. 4, pp. 657-666, Jul. 22, 2005.
S. P. Gupta et al., "Potential Anticancer Agents: Synthesis of Cytidine-5-carboxylic Acid & Cytosine-5-carbonylaminoacids", Indian Journal of Chemistry, vol. 15B, No. 5, pp. 463-465, May 1977.

* cited by examiner

*Primary Examiner* — James O Wilson
*Assistant Examiner* — Alexander R Pagano
(74) *Attorney, Agent, or Firm* — New England Biolabs, Inc; Harriet M. Strimpel

(57) ABSTRACT

The invention relates to new proteins called alkylcytosine transferases (ACTs) derived from $O^6$-alkylguanine-DNA alkyltransferase, and to substrates for ACTs specifically transferring a label to these ACTs and to fusion proteins comprising these. The substrates according of the invention are substituted cytosines of formula (I) wherein $R_1$ is an aromatic or a heteroaromatic group, or an optionally substituted unsaturated alkyl, cycloalkyl or heterocyclyl group with the double bond connected to $OCH_2$—; $R_2$ is a linker; and L is a label or a plurality of same or different labels. The invention further relates to methods of transferring label L from these substrates of formula (I) to ACTs and ACT fusion proteins. The system of ACT-compound of formula (I) is particularly suitable for double labelling studies together with the known system $O_6$-alkylguanine-DNA alkyltransferase (AGT)-benzylguanines.

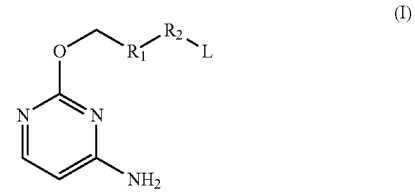

(I)

19 Claims, 3 Drawing Sheets

SEQUENCE LISTING

```
<160> NUMBER OF SEQ ID NOS: 12

<210> SEQ ID NO 1
<211> LENGTH: 182
<212> TYPE: PRT
<213> ORGANISM: artificial sequence
<220> FEATURE:
<223> OTHER INFORMATION: alkylcytosine transferase 1 derived from
      O6-alkylguanine-DNA alkyltransferase

<400> SEQUENCE: 1

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Ile
                20                  25                  30

Phe Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Ala Thr Ala
```

```
                50                  55                  60
Trp Leu Asn Ala Tyr Phe His Gln Pro Glu Ala Ile Glu Glu Phe Pro
 65                  70                  75                  80

Val Pro Ala Leu His His Pro Val Phe Gln Gln Glu Ser Phe Thr Arg
                 85                  90                  95

Gln Val Leu Trp Lys Leu Leu Lys Val Val Lys Phe Gly Glu Val Ile
                100                 105                 110

Ser Arg Ser His Leu Ala Ala Leu Ala Gly Asn Pro Ala Ala Thr Ala
                115                 120                 125

Ala Val Ser Thr Ala Leu Asp Gly Asn Pro Val Pro Ile Leu Ile Pro
            130                 135                 140

Cys His Arg Glu Val Gln Gly Asp Leu Asp Val Gly Gly Tyr Met Gly
145                 150                 155                 160

Gly Leu Ala Val Lys Glu Trp Leu Leu Ala His Glu Gly His Arg Leu
                165                 170                 175

Gly Lys Pro Gly Leu Gly
            180

<210> SEQ ID NO 2
<211> LENGTH: 182
<212> TYPE: PRT
<213> ORGANISM: artificial sequence
<220> FEATURE:
<223> OTHER INFORMATION: O6-alkylguanine-DNA alkyltransferase (AGT)
      mutant

<400> SEQUENCE: 2

Met Asp Lys Asp Cys Glu Met Lys Arg Thr Thr Leu Asp Ser Pro Leu
  1               5                  10                  15

Gly Lys Leu Glu Leu Ser Gly Cys Glu Gln Gly Leu His Glu Ile Ile
                 20                  25                  30

Phe Leu Gly Lys Gly Thr Ser Ala Ala Asp Ala Val Glu Val Pro Ala
             35                  40                  45

Pro Ala Ala Val Leu Gly Gly Pro Glu Pro Leu Met Gln Ala Thr Ala
         50                  55                  60

Trp Leu Asn Ala Tyr Phe His Gln Pro Glu Ala Ile Glu Glu Phe Pro
 65                  70                  75                  80

Val Pro Ala Leu His His Pro Val Phe Gln Gln Glu Ser Phe Thr Arg
                 85                  90                  95

Gln Val Leu Trp Lys Leu Leu Lys Val Val Lys Phe Gly Glu Val Ile
                100                 105                 110

Ser Tyr Ser His Leu Ala Ala Leu Ala Gly Asn Pro Ala Ala Thr Ala
                115                 120                 125

Ala Val Lys Thr Ala Leu Ser Gly Asn Pro Val Pro Ile Leu Ile Pro
            130                 135                 140

Cys His Arg Val Val Gln Gly Asp Leu Asp Val Gly Gly Tyr Glu Gly
145                 150                 155                 160

Gly Leu Ala Val Lys Glu Trp Leu Leu Ala His Glu Gly His Arg Leu
                165                 170                 175

Gly Lys Pro Gly Leu Gly
            180

<210> SEQ ID NO 3
<211> LENGTH: 60
<212> TYPE: DNA
<213> ORGANISM: artificial sequence
<220> FEATURE:
<223> OTHER INFORMATION: N, AGT with Sfi1 restriction site
```

```
<400> SEQUENCE: 3
ctactcgcgg cccagccggc catggcggac tacaaagaca tggacaagga ttgtgaaatg    60

<210> SEQ ID NO 4
<211> LENGTH: 45
<212> TYPE: DNA
<213> ORGANISM: artificial sequence
<220> FEATURE:
<223> OTHER INFORMATION: C, AGT with Sfi1 restriction site

<400> SEQUENCE: 4
gcaatggaat tcggcccccg aggccgctcc caagcctggc ttccc                    45

<210> SEQ ID NO 5
<211> LENGTH: 66
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (50)..(51)
<223> OTHER INFORMATION: n is a, c, g, or t

<400> SEQUENCE: 5
cactgctgcc gtggctgcgg ggttgcctgc cagggctgct aagtgagamn nagaaatcac    60
ttctcc                                                               66

<210> SEQ ID NO 6
<211> LENGTH: 69
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 6
ctgatcccgt gccacagann kgtccagggg gatttggatg tgnnknnkta cnnkggtgga    60
ctggccgtg                                                            69

<210> SEQ ID NO 7
<211> LENGTH: 69
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
```

```
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 7
ctgatcccgt gccacagann kgtccagggg gatttggatg tgnnknnkta cnnkggtgga      60
ctggccgtg                                                             69

<210> SEQ ID NO 8
<211> LENGTH: 33
<212> TYPE: DNA
<213> ORGANISM: artificial sequence
<220> FEATURE:
<223> OTHER INFORMATION: N, AGT with restriction sites BamH1 and EcoR1

<400> SEQUENCE: 8
cgaaatggat ccatggacaa ggattgtgaa atg                                  33

<210> SEQ ID NO 9
<211> LENGTH: 30
<212> TYPE: DNA
<213> ORGANISM: artificial sequence
<220> FEATURE:
<223> OTHER INFORMATION: C, AGT with restriction sites BamH1 and EcoR1

<400> SEQUENCE: 9
gcctttgaat tccttatccc aagcctggct                                      30

<210> SEQ ID NO 10
<211> LENGTH: 49
<212> TYPE: DNA
<213> ORGANISM: artificial sequence
<220> FEATURE:
<223> OTHER INFORMATION: N, AGT with restriction site NheI/BglII

<400> SEQUENCE: 10
gatcgagcta gcgctaccgg tcgccaccat ggacaaggat tgtgaaatg                 49

<210> SEQ ID NO 11
<211> LENGTH: 48
<212> TYPE: DNA
<213> ORGANISM: artificial sequence
<220> FEATURE:
<223> OTHER INFORMATION: C, AGT with restriction site NheI/BglII

<400> SEQUENCE: 11
ccaggcagat cttcccaagc ctggcttccc caaccggtgg ccttcatg                  48

<210> SEQ ID NO 12
<211> LENGTH: 182
<212> TYPE: PRT
<213> ORGANISM: artificial sequence
<220> FEATURE:
<223> OTHER INFORMATION: alyklcytosine transferase 10 derived from
      O6-alkylguanine-DNA alkyltransferase

<400> SEQUENCE: 12

Met Asp Lys Asp Cys Glu Met Lys Arg Thr Thr Leu Asp Ser Pro Leu
 1               5                  10                  15

Gly Lys Leu Glu Leu Ser Gly Cys Glu Gln Gly Leu His Glu Ile Ile
            20                  25                  30
```

-continued

```
Phe Leu Gly Lys Gly Thr Ser Ala Ala Asp Ala Val Glu Val Pro Ala
        35                  40                  45

Pro Ala Ala Val Leu Gly Gly Pro Glu Pro Leu Ile Gln Ala Thr Ala
        50                  55                  60

Trp Leu Asn Ala Tyr Phe His Gln Pro Glu Ala Ile Glu Glu Phe Pro
65                      70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
                100                 105                 110

Ser Glu Ser His Leu Ala Ala Leu Val Gly Asn Pro Ala Ala Thr Ala
                115                 120                 125

Ala Val Asn Thr Ala Leu Asp Gly Asn Pro Val Pro Ile Leu Ile Pro
        130                 135                 140

Cys His Arg Val Val Gln Gly Asp Ser Asp Val Gly Pro Tyr Leu Gly
145                 150                 155                 160

Gly Leu Ala Val Lys Glu Trp Leu Leu Ala His Glu Gly His Arg Leu
                165                 170                 175

Gly Lys Pro Gly Leu Gly
                180
```

US 8,227,602 B2

LABELLING OF FUSION PROTEINS WITH SYNTHETIC PROBES

This application is a U.S. national stage of International Application No. PCT/EP2007/057597 filed Jul. 24, 2007.

FIELD OF THE INVENTION

The present invention relates to methods of transferring a label from substrates to fusion proteins with a protein part specifically designed to accept the label, to novel specific substrates, and to novel proteins accepting the label of specific substrates suitable in such methods.

BACKGROUND OF THE INVENTION

There is a constant need for improved labelling techniques which would allow one to specifically label a protein of interest in order to isolate and/or track such protein of interest under in vitro or in vivo conditions. One particular method is disclosed in WO 02/083937 describing a method for detecting and/or manipulating a protein of interest wherein the protein is fused to $O^6$-alkylguanine-DNA alkyltransferase (AGT) and the AGT fusion protein contacted with a specific AGT substrate carrying a label, whereby the label is transferred to the fusion protein. The AGT fusion protein is then detected and optionally further manipulated using the label. Several mutants of wild type AGT were shown to be better suitable than wild type AGT (WO 2004/031404; Juillerat, A. et al., Chem. Biol. 10:313-317, 2003; Gronemeyer, T. et al., Protein Eng. Des. Sel. 19:309-316, 2006) in such a labelling method, and a wide range of substituted benzylguanines and related heteroarylmethylguanine compounds were described for use in transferring a label to the fusion proteins comprising AGT and AGT mutants (WO 2004/031405).

Simple $O^2$-benzyl-cytosines are known. Freccero, M. et al., J. Am. Chem. Soc. 125:3544-3553, 2003, obtained $O^2$-o-hydroxybenzyl cytosine on reaction of cytosine with o-quinone methide. Ward, A. D. and Baker, B. R., J. Med. Chem. 20:88-92, 1977, describe $O^2$-benzyl cytosine obtained from 2-chloro-4-aminopyridmidine and the sodium salt of benzyl alcohol.

SUMMARY OF THE INVENTION

The invention relates to new proteins called alkylcytosine transferases (ACTs) derived from $O^6$-alkylguanine-DNA alkyltransferase, and to substrates for ACTs specifically transferring a label to these ACTs and to fusion proteins comprising such ACT. The substrates according of the invention are substituted cytosines of formula (I)

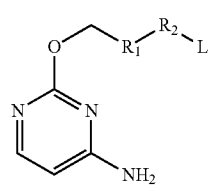

wherein
$R_1$ is an aromatic or a heteroaromatic group, or an optionally substituted unsaturated alkyl, cycloalkyl or heterocyclyl group with the double bond connected to $OCH_2$—;
$R_2$ is a linker; and
L is a label or a plurality of same or different labels.

The invention further relates to methods of transferring a label from these substrates of formula (I) to alkylcytosine transferases (ACTs) and ACT fusion proteins.

Assays were performed by incubating an equimolar mixture of GST-ACT1 and 6×His-$^N$AGT with either BGFL, BGCy5, BCFL, BCCy5 or an equimolar mixture of BGCy5/BCFL or BGFL/BCCy5. Fluorescent dye-labelled protein mixtures were analyzed by SDS-PAGE, see Example 12. GST-ACT1: fusion protein of ACT 1 (SEQ ID NO:1) with glutathione S-transferase (GST). 6×His-AGT: fusion protein of $^N$AGT (SEQ ID NO:2) with the short peptide 6×His. BGFL and BGCy5: benzylguanines substituted with a linker carrying fluorescein and Cy5, respectively, see Juillerat, A. et al., Chem. Biol. 10:313-317, 2003, and compound 11 (Example 9). BCFL: compound 5 (Example 4). BCCy5: compound 10 (Example 8).

Figure 2:
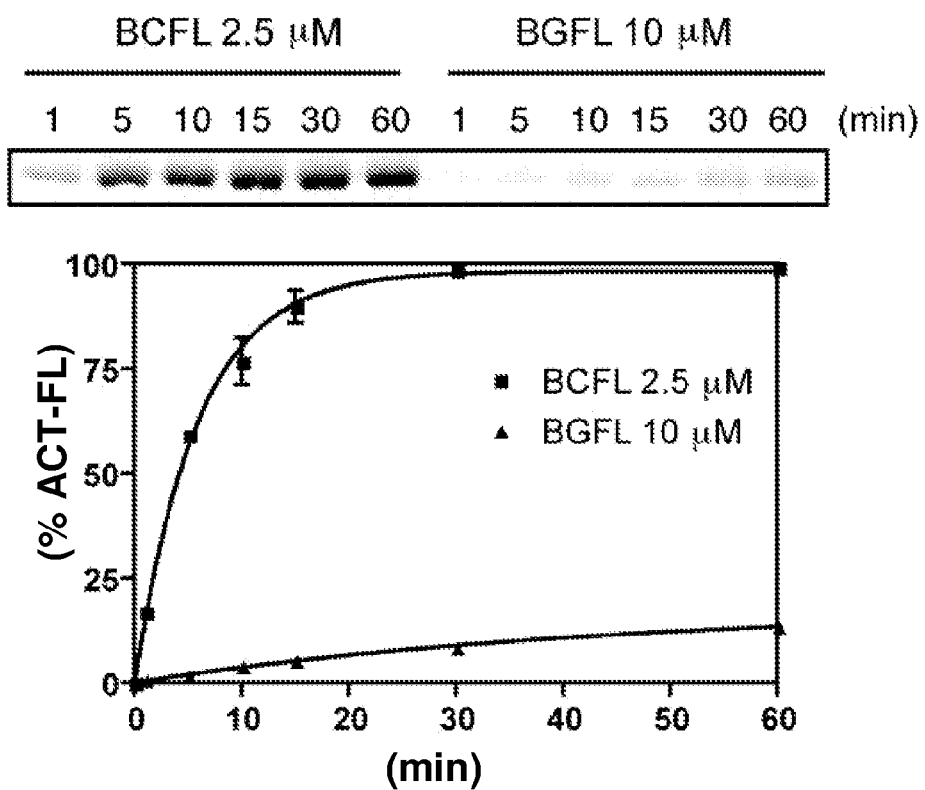

FIG. 2: Labelling experiments with ACT10 using substrates benzylguanine (BG) and benzylcytosine (BC) carrying fluorescent labels (FL) demonstrating selectivity for BC.

Figure 1:
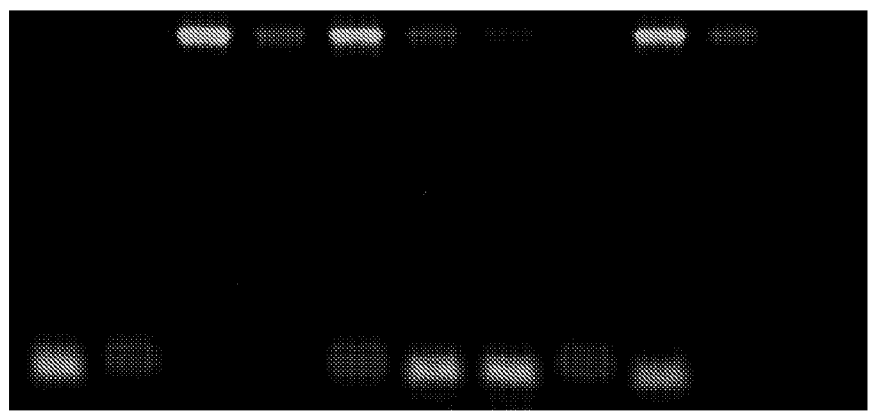
FIG. 1: In vitro dual labelling experiments with fusion proteins comprising AGT and ACT using specific substrates benzylguanine (BG) and benzylcytosine (BC) carrying fluorescent labels.

The fluorescent readout of an SDS gel run after different time of incubation is shown on top with the corresponding graph at the bottom. The percentage of ACT-Fluorescein conjugate (% ACT-FL) formed from ACT is shown vs. time of incubation (min). Assays were performed by incubating 0.5 μM mixture of GST-ACT10 with either BGFL or BCFL. GST-ACT10: fusion protein of ACT 10 (SEQ ID NO:12) with glutathione S-transferase (GST). BGFL and BCFL: see legend to FIG. 1.

Binding constants found: $k_{BC}$=1130±150 $M^{-1}s^{-1}$; $k_{BG}$~10 $M^{-1}s^{-1}$.

Figure 3:
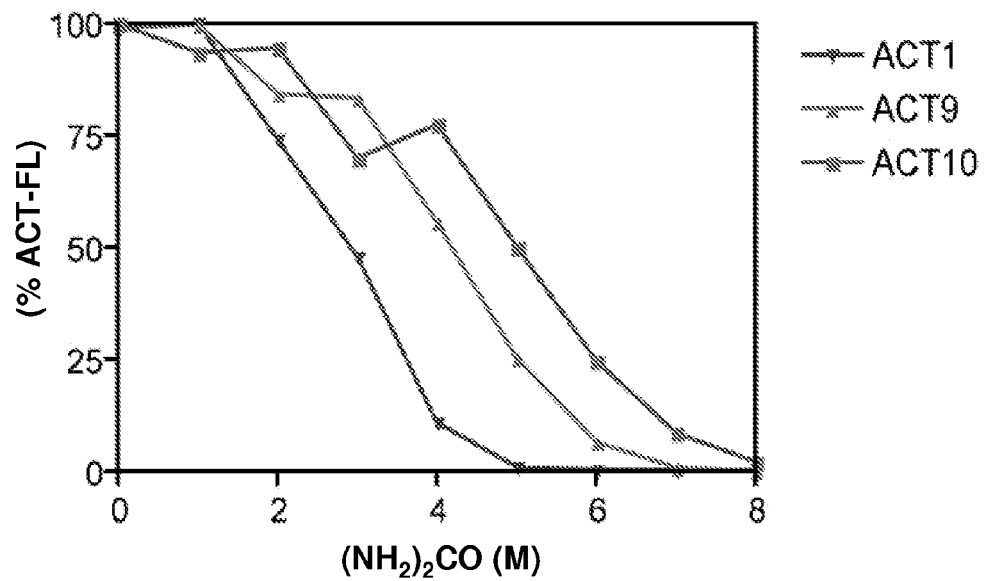

FIG. 3: Urea-induced unfolding of ACT1, ACT9 and ACT10.

Shown is the percentage of ACT-Fluorescein (% ACT-FL) formed. The value obtained at 0 M urea [$(NH_2)_2CO$] is set to 100%. Protein (0.5 μM) was incubated in kinetic buffer (50 mM HEPES, pH 7.2, 1 mM DTT) supplemented with urea (0 to 8 M) for 30 minutes. Then the solution was adjusted to 20 μM BCFL and incubated for 2 hours. Samples were then boiled 5 min at 95° C. in SDS buffer. Fluorescent dye-labelled protein mixtures were analyzed by SDS-PAGE. The data set was fitted with Y=100/(1+10^((logC1/2−X)*HillSlope)) to get the half unfolding urea concentration C1/2. The following values of C1/2 were found for the different mutants:

ACT1 2.8±0.1 M; ACT9 4.1±0.1 M; ACT10 5.1±0.2 M.

DETAILED DESCRIPTION OF THE INVENTION

The invention relates to new proteins called alkylcytosine transferases (ACTs) derived from $O^6$-alkylguanine-DNA alkyltransferase (AGT), particularly suited for the transfer of a label from substrates of formula (I).

An alkylcytosine transferase (ACT) is defined as a protein
(a) consisting of 170 to 220 amino acids, preferably 175 to 190 amino acids, most preferably 177 to 185 amino acids;
(b) comprising at least one cysteine;
(c) reacting with an $O^2$-benzylcytosine, thereby transferring the benzyl substituent to the mercapto function of cysteine of (b) at least as fast as on reaction with an $O^6$-benzylguanine under identical conditions.

ACTs of the invention were prepared from DNA encoding AGT in a directed evolution approach based on phage display of AGT. As a starting point for directed evolution based on phage display, DNA encoding the mutant $^N$AGT (SEQ ID NO:2, Gronemeyer, T. et al., Protein Eng. Des. Sel. 19:309-316, 2006) was used. $^N$AGT exhibits approximately 50-fold higher activity towards benzylguanine derivatives than wild-type $^{wt}$AGT (Juillerat, A. et al., Chem. Biol. 10:313-317, 2003) and had itself been obtained by directed evolution using phage display and a benzylguanine substrate. Codons for residues Tyr114, Lys131, Ser135, Val148, Gly156, Gly157, Glu159 were randomized via saturation mutagenesis. Transformation in phagemid pAK100 resulted in a mutant AGT library of $10^7$ independent clones. For the selection, the phage library was incubated with BCFL, a benzylcytosine carrying fluorescein (compound 5) as a substrate to label the mutants reacting with benzylcytosine. This allowed for the subsequent enrichment of the corresponding phages by using magnetic beads covered with anti-fluorescein antibodies. After 6 rounds of selection for activity against BCFL, clones ACT1 to clone ACT8 were analyzed by DNA sequencing (Table 1, amino acids shown in one-letter code). In subsequent tests it became obvious that proteins from clone ACT1 to clone ACT8 showed only limited stability against denaturation by 4 M urea. To improve this the same library was re-screened. The protein from the best isolated clone is listed as ACT9 and showed good stability in 4 M urea, but limited reactivity towards benzylcytosine. Subsequently ACT10 was obtained by error prone PCR of DNA encoding ACT9 followed by subsequent phage selection resulting in further modification of residues Met60Ile, Ala121Val and Leu153Ser as the ACT variant with high reactivity and high stability against denaturation by urea. The clones are expressed and the proteins purified as glutathione S-transferase (GST) fusion proteins.

These ten proteins specific for benzylcytosine are called alkylcytosine transferase (ACT) 1 to 10, and are the subject of the present invention.

Further proteins considered in this invention are
   ACTs which are homologs of ACT 1 to 8 and differ from ACT 1 to 8 in one, two or three amino acids in positions other than positions 114, 131, 135, 148, 157, and 159; and
   ACTs which are homologs of ACT 1 to 10 and differ from ACT 1 to 10 in one, two or three amino acids in positions other than positions 60, 114, 121, 131, 135, 148, 153, 157, and 159.
   Also considered are analogs of ACT1 (SEQ ID NO 1), in which
   the amino acid in position 114 is A, E, N, R or S;
   the amino acid in position 131 is N, S, T or V;
   the amino acid in position 135 is D, N or T;
   the amino acid in position 148 is D, E or Q;
   the amino acid in position 157 is A, G, L, T, P or W; and
   the amino acid in position 159 is E, F, M, R or S.
   Likewise considered are analogs of ACT10 (SEQ ID NO 12), in which
   the amino acid in position 60 is M or I;
   the amino acid in position 114 is A, E, N, R or S;
   the amino acid in position 121 is A or V;
   the amino acid in position 131 is N, S, T or V;
   the amino acid in position 135 is D, N or T;
   the amino acid in position 148 is D, E, Q or V;
   the amino acid in position 153 is L or S;
   the amino acid in position 157 is A, G, L, T, P or W; and
   the amino acid in position 159 is E, F, M, R, S or L.

Preferred are the proteins called alkylcytosine transferase (ACT) 1, 2, 7, 8, and 10. Particularly preferred is the protein ACT10 with the amino acid sequence shown in SEQ ID NO:12. Also preferred are homologs of ACT10 which differ thereof in one amino acid in positions other than positions 60, 114, 121, 131, 135, 148, 153, 157, and 159.

TABLE 1

Amino acid sequences of $^N$AGT and ACT 1 to 10

| | \multicolumn{9}{c}{Residue} | |
|---|---|---|---|---|---|---|---|---|---|---|
| | 60 | 114 | 121 | 131 | 135 | 148 | 153 | 157 | 159 | |
| $^N$AGT | M | Y | A | K | S | V | L | G | E | SEQ ID NO: 2 |
| ACT1 | M | R | A | S | D | E | L | G | M | SEQ ID NO: 1 |
| ACT2 | M | A | A | V | D | Q | L | W | R | |
| ACT3 | M | S | A | T | T | D | L | P | E | |
| ACT4 | M | N | A | N | D | E | L | A | S | |
| ACT5 | M | A | A | T | S | E | L | K | E | |
| ACT6 | M | E | A | R | A | E | L | E | E | |
| ACT7 | M | S | A | V | D | Q | L | L | R | |
| ACT8 | M | E | A | N | N | E | L | T | F | |
| ACT9 | M | E | A | N | D | V | L | P | F | |
| ACT10 | I | E | V | N | D | V | S | P | L | SEQ ID NO: 12 |

The invention further relates to a method for the production of alkylcytosine transferases, characterized in that a DNA encoding AGT or ACT is randomized by saturation mutagenesis in up to ten amino acid positions, the obtained library transformed into suitable phagemids, the desired phages selected by reaction with a benzylcytosine carrying a label, and phages to which the label was transferred then isolated using magnetic beads covered with antibodies directed to the label. The invention also relates to the products of such method of directed evolution.

Saturation mutagenesis is well known in the art and is, for example, accomplished as described by Dube, D. K. and Loeb, L. A., Biochemistry, 28:5703-5707, 1989.

Methods of directed evolution using phages and phagemids are also well known and are, for example, described in Smith, G. P. and Petrenko, V. A., Chem. Rev. 97:391-410, 1997; Hoess, R. H. et al., Chem. Rev. 101:3205-3218, 2001. Preferred methods use phagemids pAK100 in a system as described by Krebber, A., Bornhauser, S., Burmester, J., Honegger, A., Willuda, J., Bosshard, H. R. and Plückthun, A., J. Immunol. Methods 201:35-55, 1997.

Compounds suitable for selection of the desired clones are the substrates as described under formula (I) and being subject to this invention, in particular substrates of formula (I) wherein $R_1$ is para-substituted phenyl. The label of such a substrate being transferred to the desired ACT may be any label to which antibodies can easily be obtained, and is not restricted to a fluorescent dye label or any other spectroscopic label.

Separation using magnetic beads carrying antibodies to a particular label are also well known in the art, and are described, for example, in Gronemeyer et al., Protein Eng. Des. Sel. 19:309-316, 2006.

In a further aspect, the invention relates to compounds of formula (I)

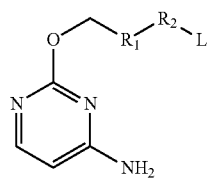

(I)

wherein

R₁ is an aromatic or a heteroaromatic group, or an optionally substituted unsaturated alkyl, cycloalkyl or heterocyclyl group with the double bond connected to OCH₂—;

R₂ is a linker; and

L is a label or a plurality of same or different labels.

R₁ as an aromatic group is preferably phenyl or naphthyl, in particular phenyl, e.g. phenyl substituted by R₂ in para or meta position.

A heteroaromatic group R₁ is a mono- or bicyclic heteroaryl group comprising zero, one, two, three or four ring nitrogen atoms and zero or one oxygen atom and zero or one sulfur atom, with the proviso that at least one ring atom is a nitrogen, oxygen or sulfur atom, and which has 5 to 12, preferably 5 or 6 ring atoms; and which in addition to carrying a substituent R₂ may be unsubstituted or substituted by one or more, especially one, further substituents selected from the group consisting of lower alkyl, such as methyl, lower alkoxy, such as methoxy or ethoxy, halogen, e.g. chlorine, bromine or fluorine, halogenated lower alkyl, such as trifluoromethyl, or hydroxy.

Preferably the mono- or bicyclic heteroaryl group R₁ is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]-pyrazolyl, thienyl, and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, e.g. 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, triazolyl, tetrazolyl, benzo[d]pyrazolyl, thienyl, and furanyl.

In a particularly preferred embodiment of the invention the heteroaryl group R₁ is thienyl, especially 2-thienyl, carrying the further substituent R₂ in 3-, 4- or 5-position, preferably 4-position, or 3-thienyl, carrying the further substituent R₂ in 4-position.

An optionally substituted unsaturated alkyl group R₁ is 1-alkenyl carrying the further substituent R₂ in 1- or 2-position, preferably in 2-position, or 1-alkynyl. Substituents considered in 1-alkenyl are e.g. lower alkyl, e.g. methyl, lower alkoxy, e.g. methoxy, lower acyloxy, e.g. acetoxy, or halogenyl, e.g. chloro. In a particularly preferred embodiment of the invention R₁ is 1-alkynyl.

An optionally substituted unsaturated cycloalkyl group is a cycloalkenyl group with 5 to 7 carbon atoms unsaturated in 1-position, e.g. 1-cyclopentenyl or 1-cyclohexenyl, carrying the further substituent R₂ in any position. Substituents considered are e.g. lower alkyl, e.g. methyl, lower alkoxy, e.g. methoxy, lower acyloxy, e.g. acetoxy, or halogenyl, e.g. chloro.

An optionally substituted unsaturated heterocyclyl group has 3 to 12 atoms, 1 to 5 heteroatoms selected from nitrogen, oxygen and sulfur, and a double bond in the position connecting the heterocyclyl group to methylene in OCH₂—. Substituents considered are e.g. lower alkyl, e.g. methyl, lower alkoxy, e.g. methoxy, lower acyloxy, e.g. acetoxy, or halogenyl, e.g. chloro.

In particular, an optionally substituted unsaturated heterocyclyl group is a partially saturated heteroaromatic group as defined hereinbefore for a heteroaromatic group R₁. An example of such a heterocyclyl group is isoxazolidinyl, especially 3-isoxazolidinyl carrying the further substituent in 5-position, or 5-isoxazolidinyl, carrying the further substituent in 3-position.

A linker group R₂ is preferably a flexible linker connecting a label L or a plurality of same or different labels L to the substrate. Linker units are chosen in the context of the envisioned application, i.e. in the transfer of the substrate to a fusion protein comprising ACT. They also increase the solubility of the substrate in the appropriate solvent. The linkers used are chemically stable under the conditions of the actual application. The linker does not interfere with the reaction with ACT nor with the detection of the label L, but may be constructed such as to be cleaved at some point in time after the reaction of the compound of formula (I) with the fusion protein comprising ACT.

A linker R₂ is a straight or branched chain alkylene group with 1 to 300 carbon atoms, wherein optionally (a) one or more carbon atoms are replaced by oxygen, in particular wherein every third carbon atom is replaced by oxygen, e.g. a polyethyleneoxy group with 1 to 100 ethyleneoxy units;

(b) one or more carbon atoms are replaced by nitrogen carrying a hydrogen atom, and the adjacent carbon atoms are substituted by oxo, representing an amide function —NH—CO—;

(c) one or more carbon atoms are replaced by oxygen, and the adjacent carbon atoms are substituted by oxo, representing an ester function —O—CO—;

(d) the bond between two adjacent carbon atoms is a double or a triple bond, representing a function —CH=CH— or —C≡C—;

(e) one or more carbon atoms are replaced by a phenylene, a saturated or unsaturated cycloalkylene, a saturated or unsaturated bicycloalkylene, a bridging heteroaromatic or a bridging saturated or unsaturated heterocyclyl group;

(f) two adjacent carbon atoms are replaced by a disulfide linkage —S—S—; or a combination of two or more, especially two or three, alkylene and/or modified alkylene groups as defined under (a) to (f) hereinbefore, optionally containing substituents.

Substituents considered are e.g. lower alkyl, e.g. methyl, lower alkoxy, e.g. methoxy, lower acyloxy, e.g. acetoxy, or halogenyl, e.g. chloro.

Further substituents considered are e.g. those obtained when an α-amino acid, in particular a naturally occurring α-amino acid, is incorporated in the linker R₂ wherein carbon atoms are replaced by amide functions —NH—CO— as defined under (b). In such a linker, part of the carbon chain of the alkylene group R₂ is replaced by a group —(NH—CHR—CO)$_n$— wherein n is between 1 and 100 and R represents a varying residue of an α-amino acid.

A further substituent is one which leads to a photocleavable linker R₂, e.g. an o-nitro-phenyl group. In particular this substituent o-nitrophenyl is located at a carbon atom adjacent to an amide bond, e.g. in a group —NH—CO—CH₂—CH(o-nitrophenyl)-NH—CO—, or as a substituent in a polyethylene glycol chain, e.g. in a group —O—CH$_2$—CH(o-nitrophenyl)-O—. Other photocleavable linkers considered are e.g. phenacyl, alkoxybenzoin, benzylthioether and pivaloyl glycol derivatives.

A phenylene group replacing carbon atoms as defined under (e) hereinbefore is e.g. 1,2-, 1,3-, or preferably 1,4-phenylene. In a particular embodiment, the phenylene group is further substituted by a nitro group, and, combined with other replacements as mentioned above under (a), (b), (c), (d), and (f), represents a photocleavable group, and is e.g. 4-nitro-1,3-phenylene, such as in —CO—NH—CH$_2$-4-nitro-1,3-phenylene-CH(CH$_3$)—O—CO—, or 2-methoxy-5-nitro-1,4-phenylene, such as in —CH$_2$—O-2-methoxy-5-nitro-1,4-phenylene-CH(CH$_3$)—O—. Other particular embodiments representing photocleavable linkers are e.g. -1,4-phenylene-CO—CH$_2$—O—CO—CH$_2$— (a phenacyl group), -1,4-phenylene-CH(OR)—CO-1,4-phenylene- (an alkoxybenzoin), or -3,5-dimethoxy-1,4-phenylene-CH$_2$—O— (a dimethoxybenzyl moiety). A saturated or unsaturated cycloalkylene group replacing carbon atoms as defined under (e) hereinbefore is derived from cycloalkyl with 3 to 7 carbon atoms, preferably from cyclopentyl or cyclohexyl, and is e.g. 1,2- or 1,3-cyclopentylene, 1,2-, 1,3-, or preferably 1,4-cyclohexylene, or also 1,4-cyclohexylene being unsaturated e.g. in 1- or in 2-position. A saturated or unsaturated bicycloalkylene group replacing carbon atoms as defined under (e) hereinbefore is derived from bicycloalkyl with 7 or 8 carbon atoms, and is e.g. bicyclo[2.2.1]heptylene or bicyclo[2.2.2]octylene, preferably 1,4-bicyclo[2.2.1]heptylene optionally unsaturated in 2-position or doubly unsaturated in 2- and 5-position, and 1,4-bicyclo[2.2.2]octylene optionally unsaturated in 2-position or doubly unsaturated in 2- and 5-position. A bridging heteroaromatic group replacing carbon atoms as defined under (e) hereinbefore is e.g. triazolidene, preferably 1,4-triazolidene, or isoxazolidene, preferably 3,5-isoxazolidene. A bridging saturated or unsaturated heterocyclyl group replacing carbon atoms as defined under (e) hereinbefore is e.g. derived from an unsaturated heterocyclyl group as defined under R$_1$ above, e.g. isoxazolidinene, preferably 3,5-isoxazolidinene, or a fully saturated heterocyclyl group with 3 to 12 atoms, 1 to 3 of which are heteroatoms selected from nitrogen, oxygen and sulfur, e.g. pyrrolidinediyl, piperidinediyl, tetrahydrofuranediyl, dioxanediyl, morpholinediyl or tetrahydrothiophenediyl, preferably 2,5-tetrahydrofuranediyl or 2,5-dioxanediyl. A particular heterocyclyl group considered is a saccharide moiety, e.g. an α- or β-furanosyl or α- or β-pyranosyl moiety.

Cyclic substructures in a linker R$_2$ reduce the molecular flexibility as measured by the number of rotatable bonds within R$_2$, which leads to a better membrane permeation rate, important for all in vivo labelling applications.

A linker R$_2$ is preferably a straight chain alkylene group with 1 to 25 carbon atoms or a straight chain polyethylene glycol group with 4 to 100 ethyleneoxy units, optionally attached to the group R$_1$ by a —CH═CH— or —C≡C— group. Further preferred is a straight chain alkylene group with 1 to 25 carbon atoms wherein carbon atoms are optionally replaced by an amide function —NH—CO—, and optionally carrying a photocleavable subunit, e.g. o-nitrophenyl. Further preferred are branched linkers comprising a polyethylene glycol group of 3 to 6 ethylene glycol units and alkylene groups wherein carbon atoms are replaced by amide bonds, and further carrying substituted amino and hydroxy functions. Other preferred branched linkers have dendritic (tree-like) structures wherein amine, carboxamide and/or ether functions replace carbon atoms of an alkylene group.

A particularly preferred linker R$_2$ is a straight chain alkylene group of 2 to 20 carbon atoms wherein one or two carbon atoms are replaced by nitrogen and which is optionally substituted by oxo adjacent to the nitrogen.

Another particularly preferred linker R$_2$ is a straight chain alkylene group of 10 to 40 carbon atoms optionally substituted by oxo wherein 3 to 12 carbon atoms are replaced by oxygen and one or two carbon atoms are replaced by nitrogen, optionally substituted by oxo adjacent to nitrogen.

A linker R$_2$ may carry one or more same or different labels, e.g. 1 to 100 same or different labels, in particular 1 to 5, preferably one, two or three, in particular one or two same or different labels.

Lower alkyl is alkyl with 1 to 7, preferably from 1 to 4 C atoms, and is linear or branched; preferably, lower alkyl is butyl, such as n-butyl, sec-butyl, isobutyl, tert-butyl, propyl, such as n-propyl or isopropyl, ethyl or methyl. Most preferably, lower alkyl is methyl.

In lower alkoxy, the lower alkyl group is as defined hereinbefore. Lower alkoxy denotes preferably n-butoxy, tert-butoxy, iso-propoxy, ethoxy, or methoxy, in particular methoxy.

In lower acyloxy, lower acyl has the meaning of formyl or lower alkylcarbonyl wherein lower alkyl is defined as hereinbefore. Lower acyloxy denotes preferably n-butyroxy, n-propionoxy, iso-propionoxy, acetoxy, or formyloxy, in particular acetoxy.

Halogen is fluoro, chloro, bromo or iodo, in particular chloro.

The label L of the substrate can be chosen by those skilled in the art dependent on the application for which the fusion protein is intended. Labels are such that the labelled fusion protein carrying label L is easily detected or separated from its environment. Other labels considered are those which are capable of sensing and inducing changes in the environment of the labelled fusion protein and/or the substrate, or labels which aid in manipulating the fusion protein by the physical and/or chemical properties of the substrate and specifically introduced into the fusion protein. A label as understood in the context of the invention is a substituent different from hydrogen or from standard functional groups, in particular different from hydrogen, hydroxy, amino, halogen, carboxylate, carboxamide, carboxylic ester, nitrile, cyanate, isocyanate, sulfonate, sulfonamide, sulfonic ester, aldehyde, ketone, ether, and thioether substituent.

Examples of a label include a spectroscopic probe such as a fluorophore or a chromophore, a magnetic probe or a contrast reagent; a radioactively labelled molecule; a molecule which is one part of a specific binding pair which is capable of specifically binding to a partner; a molecule that is suspected to interact with other biomolecules; a library of molecules that are suspected to interact with other biomolecules; a molecule which is capable of crosslinking to other molecules; a molecule which is capable of generating hydroxyl radicals upon exposure to H$_2$O$_2$ and ascorbate, such as a tethered metal-chelate; a molecule which is capable of generating reactive radicals upon irradiation with light, such as malachite green; a molecule covalently attached to a solid support, where the support may be a glass slide, a microtiter plate or any polymer known to those proficient in the art; a nucleic acid or a derivative thereof capable of undergoing base-pairing with its complementary strand; a lipid or other hydrophobic molecule with membrane-inserting properties; a biomolecule with desirable enzymatic, chemical or physical properties; or a molecule possessing a combination of any of the properties listed above.

Further labels L are positively charged linear or branched polymers which are known to facilitate the transfer of attached molecules over the plasma membrane of living cells. This is of particular importance for substances which otherwise have a low cell membrane permeability or are in effect impermeable for the cell membrane of living cells. A non cell permeable ACT substrate will become cell membrane permeable upon conjugation to such a group L. Such cell membrane transport enhancer groups L comprise, for example, a linear poly(arginine) of D- and/or L-arginine with 6-15 arginine residues, linear polymers of 6-15 subunits which each carry a guanidinium group, oligomers or short-length polymers of from 6 to up to 50 subunits, a portion of which have attached guanidinium groups, and/or parts of the sequence of the HIV-tat protein, in particular the subunit Tat49-Tat57 (RKKRRQRRR in the one letter amino acid code). The ACT substrate is covalently linked to this group L through a linker $R_2$ as defined hereinbefore, which is preferably labile inside a living cell and may be degraded, e.g. by cleavage of an ester group $R_2$ by intracellular esterases, leading directly or in a further reaction provoked by the cleavage of the ester function to a separation of the ACT substrate and the unit L enhancing cell membrane permeability.

Preferred as labels L are spectroscopic probes, and molecules which are one part of a specific binding pair which is capable of specifically binding to a partner, so-called affinity labels. Also preferred as labels L are molecules covalently attached to a solid support. Preferred spectroscopic probes are fluorophores.

When the label L is a fluorophore, a chromophore, a magnetic label, a radioactive label or the like, detection is by standard means adapted to the label and whether the method is used in vitro or in vivo. If L is a fluorophore the method can be compared to the applications of the green fluorescent protein (GFP) which is genetically fused to a protein of interest and allows protein investigation in the living cell. Particular examples of labels L are also boron compounds displaying non-linear optical properties. Particularly preferred are labels such that L of one substrate ($L_1$) is one member and L of another substrate ($L_2$) is the other member of two interacting spectroscopic probes $L_1/L_2$, wherein energy can be transferred nonradiatively between the donor and acceptor (quencher) when they are in close proximity (less than 10 nanometer distance) through either dynamic or static quenching. Such a pair of labels $L_1/L_2$ changes its spectroscopic properties on reaction of the labelled substrate carrying $L_1$ with the ACT fusion protein and another type of labelled substrate (e.g. a benzylguanine type) carrying $L_2$ with another corresponding fusion protein, e.g. an AGT fusion protein. An example of such a pair of labels $L_1/L_2$ is a FRET pair explained below in more detail.

Particular fluorophores considered are: Alexa Fluor dyes, including Alexa Fluor 350, 488, 532, 546, 555, 635 and 647 (Invitrogen Corp., Carlsbad, Calif. 92008, USA, see also Panchuk-Voloshina, N. et al., J. Histochem. & Cytochem. 47:1179-1188, 1999); coumarins such as 7-dimethylamino-coumarin-4-acetic acid (succinimidyl ester supplied as product D374 by Invitrogen Molecular Probes), 7-amino-4-methyl-coumarin-3-acetic acid and 7-diethylamino-coumarin-3-carboxylic acid; Cyanine-3 (Cy 3), Cyanine 5 (Cy 5) and Cyanine 5.5 (Cy 5.5) (Amersham-GE Healthcare, Solingen, Germany); ATTO 488, ATTO 532, ATTO 600 and ATTO 655 (Atto-Tec, D57076 Siegen, Germany); DY-505, DY-547, DY-632 and DY-647 (Dyomics, Jena, Germany); and 5(6)-carboxyfluorescein and difluoro-5(6)-carboxyfluorescein (Oregon Green). These particular labels on the substrate of formula (I) may be combined with the known AGT-benzylguanine system wherein the label on the benzylguanine is a quencher to create a FRET pair with the fluorophore on the substrate of formula (I) reacting with ACT. Such quenchers are: QSY 35, QSY 9 and QSY 21 (Invitrogen Molecular Probes); BHQ-1, BHQ-2 and BHQ-3 (Black Hole Quencher™ of Biosearch Technologies, Inc., Novato, Calif. 94949, USA); ATTO 540Q and ATTO 612Q (Atto-Tec, D57076 Siegen, Germany); 4-dimethylamino-azobenzene-4'-sulfonyl derivatives (Dabsyl) and 4-dimethylaminoazobenzene-4'-carbonyl derivatives (Dabcyl).

Depending on the properties of the label L, the fusion protein comprising protein of interest and ACT may be bound to a solid support on reaction with the substrate. The label L of the substrate reacting with the fusion protein comprising ACT may already be attached to a solid support when entering into reaction with ACT, or may subsequently, i.e. after transfer to ACT, be used to attach the labelled ACT fusion protein to a solid support. The label may be one member of a specific binding pair, the other member of which is attached or attachable to the solid support, either covalently or by any other means. A specific binding pair considered is e.g. biotin and avidin or streptavidin. Either member of the binding pair may be the label L of the substrate, the other being attached to the solid support. Further examples of labels allowing convenient binding to a solid support are e.g. maltose binding protein, glycoproteins, FLAG tags, or reactive substituents allowing chemoselective reaction between such substituent with a complementary functional group on the surface of the solid support. Examples of such pairs of reactive substituents and complementary functional group are e.g. amine and activated carboxy group forming an amide, azide and a propiolic acid derivative undergoing a 1,3-dipolar cycloaddition reaction, amine and another amine functional group reacting with an added bifunctional linker reagent of the type of activated bis-dicarboxylic acid derivative giving rise to two amide bonds, or other combinations known in the art.

Examples of a convenient solid support are e.g. glass surfaces such as glass slides, microtiter plates, and suitable sensor elements, in particular functionalized polymers (e.g. in the form of beads), chemically modified oxidic surfaces, e.g. silicon dioxide, tantalum pentoxide or titanium dioxide, or also chemically modified metal surfaces, e.g. noble metal surfaces such as gold or silver surfaces. Irreversibly attaching and/or spotting ACT substrates may then be used to attach ACT fusion proteins in a spatially resolved manner, particularly through spotting, on the solid support representing protein microarrays, DNA microarrays or arrays of small molecules.

When the label L is capable of generating reactive radicals, such as hydroxyl radicals, upon exposure to an external stimulus, the generated radicals can then inactivate the ACT fusion proteins as well as those proteins that are in close proximity of the ACT fusion protein, allowing to study the role of these proteins. Examples of such labels are tethered metal-chelate complexes that produce hydroxyl radicals upon exposure to $H_2O_2$ and ascorbate, and chromophores such as malachite green that produce hydroxyl radicals upon laser irradiation. The use of chromophores and lasers to generate hydroxyl radicals is also known in the art as chromophore assisted laser induced inactivation (CALI). In the present invention, labelling ACT fusion proteins with substrates carrying chromophores as label L, such as malachite green, and subsequent laser irradiation inactivates the labelled ACT fusion protein as well as those proteins that interact with the ACT fusion protein in a time-controlled and spatially-resolved manner. This method can be applied both in vivo or in vitro. Furthermore, proteins which are in close proximity of the ACT fusion protein can be identified as such by either detecting fragments of that protein by a specific antibody, by the disappearance of those proteins on a high-resolution 2D-electrophoresis gels or by identification of the cleaved protein fragments via separation and sequencing techniques such as mass spectrometry or protein sequencing by N-terminal degradation.

When the label L is a molecule that can cross-link to other proteins, e.g. a molecule containing functional groups such as maleimides, active esters or azides and others known to those proficient in the art, contacting such labelled ACT substrates with ACT fusion proteins that interact with other proteins (in vivo or in vitro) leads to the covalent cross-linking of the ACT fusion protein with its interacting protein via the label. This allows the identification of the protein interacting with the ACT fusion protein. Labels L for photo cross-linking are e.g. benzophenones. In a special aspect of cross-linking the label L is a molecule which is itself an ACT substrate leading to dimerization of the ACT fusion protein. The chemical structure of such dimers may be either symmetrical (homodimers) or unsymmetrical (heterodimers).

Other labels L considered are for example fullerenes, boranes for neutron capture treatment, nucleotides or oligonucleotides, e.g. for self-addressing chips, peptide nucleic acids, and metal chelates, e.g. platinum chelates that bind specifically to DNA.

A particular biomolecule with desirable enzymatic, chemical or physical properties is methotrexate. Methotrexate is a tight-binding inhibitor of the enzyme dihydrofolate reductase (DHFR). Compounds of formula (I) wherein L is methotrexate belong to the well known class of so-called "chemical inducers of dimerization" (CIDs). Using fusion proteins of ACT with the DNA-binding domain LexA, and adding DHFR with the transcriptional activation domain B42 to the in vivo labeling of the ACT fusion protein with a compound of formula (I) wherein L is methotrexate induces the coupling ("dimerization") of the ACT-LexA fusion protein and DHFR-B42 fusion protein, leading to spatial proximity of LexA and B42 and subsequent stimulation of transcription.

If the substrate carries two or more labels, these labels may be identical or different. Particular preferred combinations are two different affinity labels, or one affinity label and one chromophore label, in particular one affinity label and one fluorophore label, or a pair of spectroscopic interacting labels $L_1/L_2$, e.g. a FRET pair.

Preferred are compounds of formula (I) wherein $R_1$ is phenyl, in particular para-substituted phenyl.

Preferred are compounds of formula (I) wherein L is a spectroscopic probe, e.g. a fluorophore. Likewise preferred are compounds wherein L is a molecule representing one part of a specific binding pair, and compounds wherein L is a molecule covalently attached to a solid support.

Most preferred are the compounds of the Examples.

The invention further relates to a method for detecting and/or manipulating a protein of interest, wherein the protein of interest is incorporated into an ACT fusion protein, the ACT fusion protein is contacted with a compound of formula (I) carrying a label as described hereinbefore, and the ACT fusion protein is detected and optionally further manipulated using the label in a system designed for recognising and/or handling the label.

In the method of the present invention a protein or peptide of interest is fused to an ACT. The protein or peptide of interest may be of any length and both with and without secondary, tertiary or quaternary structure, and preferably consists of at least twelve amino acids and up to 2000 amino acids. Examples of such protein or peptide of interest are e.g. enzymes, DNA-binding proteins, transcription regulating proteins, membrane proteins, nuclear receptor proteins, nuclear localization signal proteins, protein cofactors, small monomeric GTPases, ATP-binding cassette proteins, intracellular structural proteins, proteins with sequences responsible for targeting proteins to particular cellular compartments, proteins generally used as labels or affinity tags, and domains or subdomains of the aforementioned proteins. The protein or peptide of interest is preferably fused to ACT by way of a linker which may be cleaved by an enzyme, e.g. at the DNA stage by suitable restriction enzymes and/or linkers cleavable by suitable enzymes at the protein stage.

The ACT has the property of transferring a label present on a substrate, i.e. on the compound of formula (I), to one of the cysteine residues of the ACT forming part of a fusion protein. In preferred embodiments, the ACT is selected from the group consisting of ACT 1 to ACT 10 as defined hereinbefore, and homologs thereof. Particularly preferred is ACT 10.

The fusion protein comprising protein of interest and an ACT is contacted with a particular substrate of formula (I). Conditions of reaction are selected such that the ACT reacts with the substrate and transfers the label of the substrate. Usual conditions are a buffer solution at around pH 7 at room temperature, e.g. around 25° C. However, it is understood that ACT reacts also under a variety of other conditions, and those conditions mentioned here are not limiting the scope of the invention.

The label L of the substrate is chosen by those skilled in the art dependent on the application for which the fusion protein is intended. After contacting the fusion protein comprising ACT with the substrate, the label L is covalently bonded to the fusion protein. The labelled ACT fusion protein is then further manipulated and/or detected by virtue of the transferred label. The label L may consist of a plurality of same or different labels. If the substrate contains more than one label L, the corresponding labelled ACT fusion protein will also comprise more than one label which gives more options for further manipulating and/or detecting the labelled fusion protein.

"Detected" in the sense of the present invention means that the fusion protein with ACT carrying label L can be localised due to the properties of the label, and the amount of fusion protein determined either directly or by reference to a standard. "Manipulated" in the sense of the present invention means that the fusion protein with ACT carrying label L can be reacted further due to the properties of the label, e.g. isolated from the in vitro or in vivo system, enriched and purified, i.e. separated from other proteins and/or non-proteinaceous material, brought in solution (e.g. especially if the fusion protein is not soluble), precipitated (e.g. especially if the fusion protein is soluble) or otherwise fixed to a solid, and also further treated e.g. by cleaving the linker which splits off the label and regenerates the fusion protein. The skilled person well understands the many possibilities for further handling the fusion protein carrying label L due to the properties of the label L and of the linker $R_2$ connecting L to the fusion protein.

In vitro, the reaction of the ACT fusion protein with the substrate of the invention can generally be either performed in cell extracts or with purified or enriched forms of the ACT fusion protein.

If experiments with the substrates of the present invention are done in vivo or in cell extracts, the reaction of the endogenous AGT will not disturb the reaction of an ACT fusion protein with a substrate of the formula (I), since said substrate does not (or at least not detectably) interact with endogenous AGT, only with ACT. This is a substantial advantage of the present combination ACT-substrate of formula (I) over the standard combination of AGT-benzylguanine type substrate described in the prior art.

Particular fluorophores labels on the substrate of formula (I) as described hereinbefore may be combined with the known AGT-benzylguanine system wherein the label on the benzylguanine is a quencher to create a FRET pair with the fluorophore on the substrate of formula (I) reacting with ACT. Preferred are the quenchers listed hereinbefore as labels L for substrates of formula (I).

Alternatively, the label L on the substrate of formula (I) may be one of the quenchers mentioned above, and the reaction with ACT accomplished in a mixture with a AGT fusion protein-benzylguanine substrate combination wherein the label on benzylguanine is one of the mentioned fluorophores.

Substrates of the invention are generally prepared by standard methods known in the art. A useful starting material is 2-chloropyrimidin-4-amine or another cytosine derivative with an activated leaving group at position 2 of the pyrimidine ring. This compound is then reacted with an alcohol of formula HO—$CH_2$—$R_1$—$R_2$-L or an analogous compound HO—$CH_2R_1$—$R_2'$ wherein $R_2'$ is precursor of a linker $R_2$ allowing the introduction of a label L and thereby completing the residue $R_2$-L. Particular useful precursor $R_2'$ are those with an amino function, which allows a condensation reaction with labels carrying a carboxyl function, e.g. in the form of a succinimidyl ester giving rise to linker $R_2$ incorporating an amide function.

Appropriate protecting groups for the envisioned functionalities can be chosen by those skilled in the art, and are e.g. summarized in Greene, T. W. and Wuts, P. G. M. in "Protective Groups in Organic Synthesis", John Wiley & Sons, New York 1991.

The invention further relates to methods of transferring a label from these substrates of formula (I) to alkylcytosine transferases (ACTs) and ACT fusion proteins.

The combination ACT-substrate of formula (I) is particularly suitable for tracing two different proteins in combination with the known AGT-benzylguanine type substrate, since the substrate of formula (I) and benzylguanine type substrates transfer their labels selectively to ACT and AGT fusion proteins, respectively.

In order to demonstrate the feasibility of specific dual labelling using ACTs, an equimolar mixture of hexahistidine tagged $^N$AGT (6×His-$^N$AGT) and GST-ACT1 fusion protein was incubated with either BGFL, BGCy5, BCFL, BCCy5 or an equimolar mixture of BGCy5/BCFL or BGFL/BCCy5. Incubation with BGFL or BGCy5 led to a complete labelling of 6×His-$^N$AGT and very low labelling of GST-ACT1 (estimated to be less than 5% in both case). In an opposite way, incubation with BCFL or BCCy5 led to a complete labelling of GST-ACT1 and a partial labelling of 6×His-$^N$AGT (76% and 6%, respectively). However, incubation with an equimolar mixture of BGCy5/BCFL (or BGFL/BCCy5) led to specific dual colour labelling, i.e. specific labelling of 6×His-$^N$AGT with Cy5 dye (or fluorescein, respectively) and specific labelling of GST-ACT1 with fluorescein (or Cy5 dye, respectively). In both case, cross labelling had been evaluated to be less than 1%.

TABLE 2

Activity of $^N$AGT and ACT 1 to 10 as GST-fusion protein with BCFL and BGFL

| | [$s^{-1} \cdot M^{-1}$] | |
|---|---|---|
| | $k_{BCFL}$ | $k_{BGFL}$ |
| $^N$AGT | 26 | 28000 |
| ACT 1 | 730 | <10 |
| ACT 2 | 330 | <10 |
| ACT 3 | 100 | n.d. |
| ACT 4 | <100 | n.d. |
| ACT 5 | 350 | 210 |
| ACT 6 | 460 | 160 |
| ACT 7 | 260 | <10 |
| ACT 8 | 600 | <10 |
| ACT 9 | 90 | <1 |
| ACT 10 | 1130 | 10 | n.d.: not determined

EXAMPLES

Abbreviations

BC=Benzylcytosine
BG=Benzylguanine
DTT=Dithiothreitol
DMF=Dimethylformamide
MPLC=Medium pressure liquid chromatography
PBS=Phosphate buffered saline
RT=Room temperature
TFA=Trifluoroacetic acid
TEA=Triethylamine Example 1

N-(4-((4-Aminopyrimidin-2-yloxy)methyl)benzyl)-2,2,2-trifluoroacetamide (1)

760 mg (3.25 mmol) 2,2,2-Trifluoro-N-(4-hydroxymethyl-benzyl)-acetamide is dissolved in 3 mL dry dimethylacetamide under argon atmosphere, and 273 mg (8.15 mmol) NaH is added over 5 min. 211 mg (1.63 mmol) 2-Chloropyrimidin-4-amine is then added and the solution stirred at 90° C. over night. 1 mL Water is added carefully to quench all excess NaH, and the mixture poured into 50 ml of 0.5 N HCl. The crude product is extracted with ethyl acetate, the combined organic phases washed with brine and dried over $MgSO_4$. After evaporation of the solvent, the product is purified by flash column chromatography (gradient ethyl acetate: cyclohexane from 1:1 to 3:1). Yield: 350 mg (52%). ESI-MS m/z 327 [M+H]$^+$.

Example 2

2-(4-(Aminomethyl)benzyloxy)4-aminopyrimidine (2)

150 mg (0.46 mmol) of N-(4-((4-Aminopyrimidin-2-yloxy)methyl)benzyl)-2,2,2-trifluoro-acetamide (1) is dissolved in 2 mL methanol and treated with 5 mL methylamine (33% in ethanol). The reaction mixture is stirred at room temperature over night and all volatiles are removed in vacuo. The product is used without further purification in the next step. ESI-MS m/z 231 [M+H]$^+$.

Example 3

N-[4-(4-Aminopyrimidin-2-yloxymethyl)-benzyl]-tetramethylrhodamine-6-carboxamide (3) and N-[4-(4-Aminopyrimidin-2-yloxymethyl)-benzyl]-tetramethylrhodamine-5-carboxamide (4)

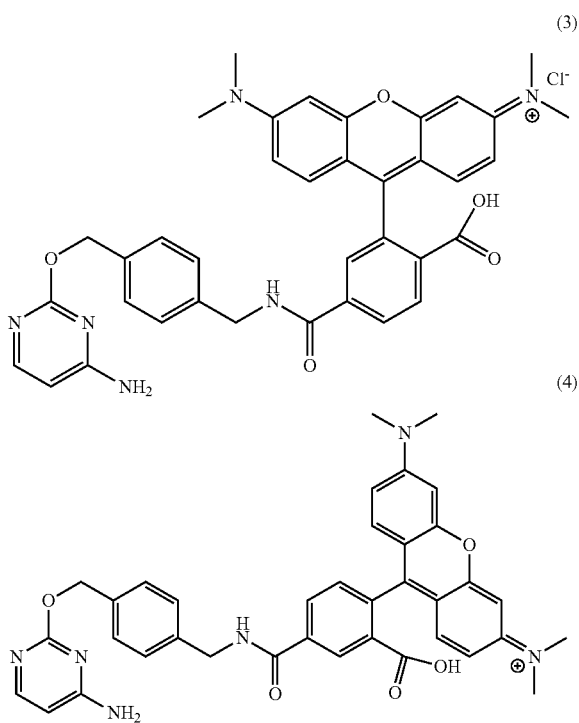

2-(4-(Aminomethyl)benzyloxy)pyrimidin-4-amine (2) (3.6 mg, 0.016 mmol) and 5(6)-carboxytetramethylrhodamine succinimidyl ester (8.2 mg, 0.016 mmol) are dissolved in 800 µL DMF with 2.4 µL TEA and heated overnight at 31° C. The solvent is evaporated in vacuo and the compounds are isolated by reversed phase MPLC (medium pressure liquid chromatography) on a C18 column using a linear gradient of water:acetonitrile (from 95:5 to 20:80 in 20 min, 0.08% TFA). MS (ESI) m/z 643 [M−Cl]$^+$.

Example 4

N-[4-(4-Aminopyrimidin-2-yloxymethyl)-benzyl]-fluorescein-6-carboxamide (5), BCFL

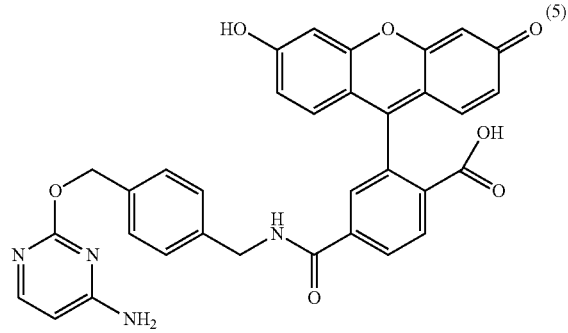

2-(4-(Aminomethyl)benzyloxy)pyrimidin-4-amine (2) (3.9 mg, 0.017 mmol) and 5(6)-carboxyfluorescein succinimidyl ester (8.3 mg, 0.017 mmol) are dissolved in 800 µL DMF with 2.6 µL TEA and heated overnight at 31° C. The solvent is evaporated in vacuo and the product is isolated by reversed phase MPLC on a C18 column using a linear gradient of water:acetonitrile (from 95:5 to 20:80 in 20 min, 0.08% TFA). MS (ESI) m/z 589 [m+H]$^+$. Depending on the purification method, the product may also contain the corresponding isomer 5-carboxamide.

Example 5

N-[4-(4-Aminopyrimidin-2-yloxymethyl)-benzyl]-diacetylfluorescein-6-carboxamide (6) and N-[4-(4-Aminopyrimidin-2-yloxymethyl)-benzyl]-diacetylfluorescein-5-carboxamide (7)

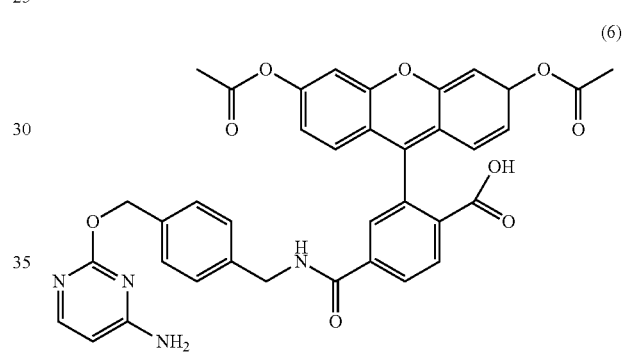

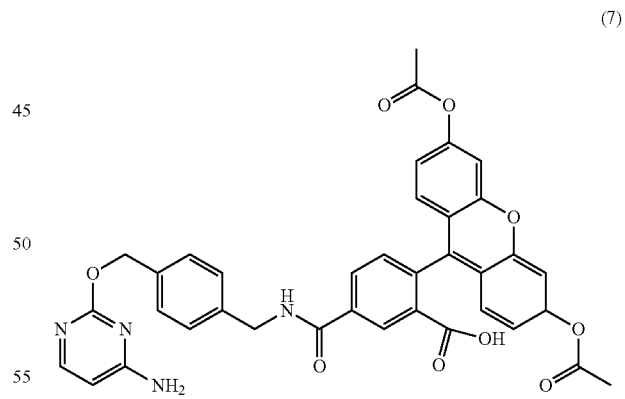

2-(4-(Aminomethyl)benzyloxy)pyrimidin-4-amine (2) (4.1 mg, 0.018 mmol) and 5(6)-carboxyfluorescein diacetate succinimidyl ester (10 mg, 0.018 mmol) are dissolved in 800 µL DMF with 2.7 µL TEA and heated overnight at 31° C. The solvent is evaporated under vacuum and the compounds isolated by reversed phase MPLC on a C18 column using a linear gradient of water:acetonitrile (from 95:5 to 20:80 in 20 min, 0.08% TFA). MS (ESI) m/z 673 [m+H]$^+$.

Example 6

N-[4-(4-Aminopyrimidin-2-yloxymethyl)-benzyl]-DY647-carboxamide (8)

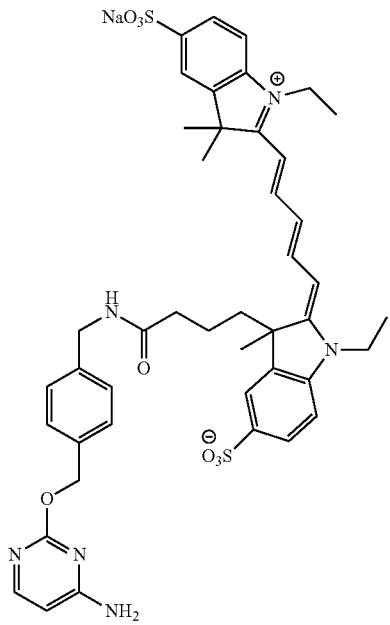

(8)

2-(4-(Aminomethyl)benzyloxy)pyrimidin-4-amine (2) (1.5 mg, 0.007 mmol) and DY-547-NHS (Dyomics dye) (5 mg, 0.007 mmol) are dissolved in 500 μL DMF with 1.0 μL TEA and heated overnight at 31° C. The solvent is evaporated under vacuum and the product is isolated by reversed phase MPLC on a C18 column using a linear gradient of water:acetonitrile (from 95:5 to 20:80 in 20 min, 0.08% TFA). MS (ESI) m/z 853 [M−Na]⁻.

Example 7

N-[4-(4-Aminopyrimidin-2-yloxymethyl)-benzyl]-DY547-carboxamide (9)

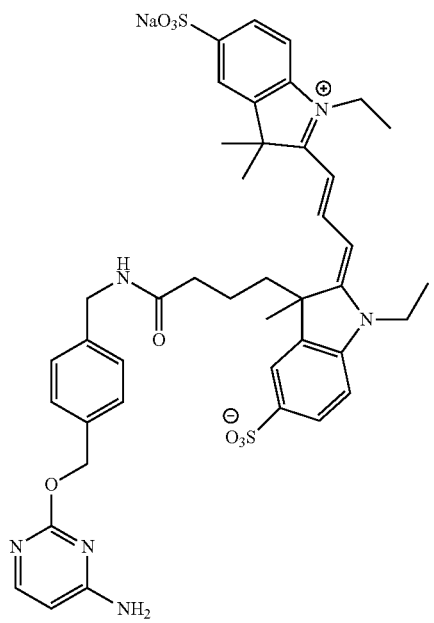

(9)

2-(4-(Aminomethyl)benzyloxy)pyrimidin-4-amine (2) (1.5 mg, 0.007 mmol) and DY-547-NHS (Dyomics dye) (5 mg, 0.007 mmol) are dissolved in 500 μL DMF with 1.0 μL TEA and heated overnight at 31° C. The solvent is evaporated under vacuum and the product is isolated by reversed phase MPLC on a C18 column using a linear gradient of water:acetonitrile (from 95:5 to 20:80 in 20 min, 0.08% TFA). MS (ESI) m/z 827 [M−Na]⁻.

Example 8

N-[4-(4-Aminopyrimidin-2-yloxymethyl)-benzyl]-Cy5-carboxamide (10) BCCy5

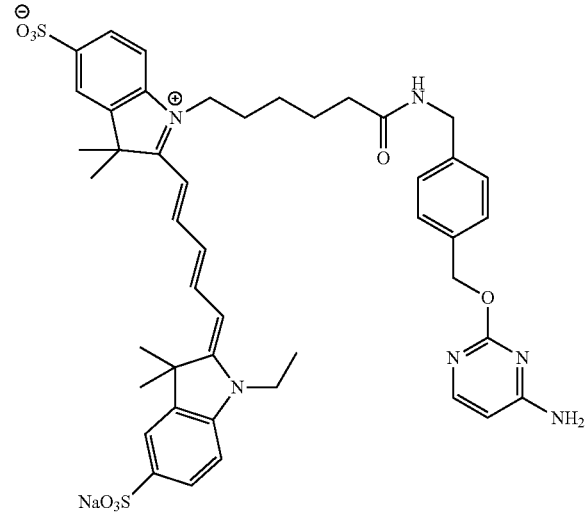

(10)

2-(4-(Aminomethyl)benzyloxy)pyrimidin-4-amine (2) (1.5 mg, 0.007 mmol) and Cy5-NHS (GE healthcare dye) (5.4 mg, 0.007 mmol) are dissolved in 500 μL DMF with 1.0 μL TEA and heated overnight at 31° C. The solvent is evaporated under vacuum and the product is isolated by reversed phase MPLC on a C18 column using a linear gradient of water:acetonitrile (from 95:5 to 20:80 in 20 min, 0.08% TFA). MS (ESI) m/z 868 [M−Na]⁻.

Example 9

O⁶-[4-(Cy5)-Aminomethyl]-benzyl guanine (11), BGCy5

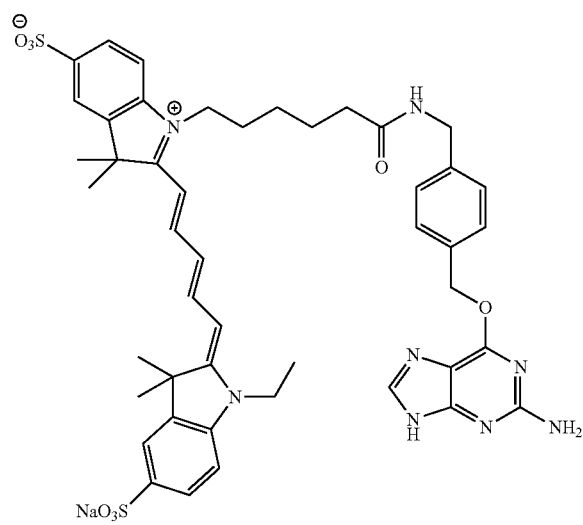

(11)

O⁶-4-aminomethyl-benzyl-guanine (1.9 mg, 0.007 mmol) and Cy5-NHS (GE healthcare dye) (5.4 mg, 0.007 mmol) are dissolved in 500 μL DMF with 1.0 μL TEA and heated overnight at 31° C. The solvent is evaporated under vacuum and the product is isolated by reversed phase MPLC on a C18 column using a linear gradient of water:acetonitrile (from 95:5 to 20:80 in 20 min, 0.08% TFA). MS (ESI) m/z 908 [M−Na]⁻.

Example 10

The following compounds are prepared from 2-(4-(aminomethyl)benzyloxy)pyrimidin-4-amine (2) in analogy to Example 3:

BC-Biotin of formula 12:

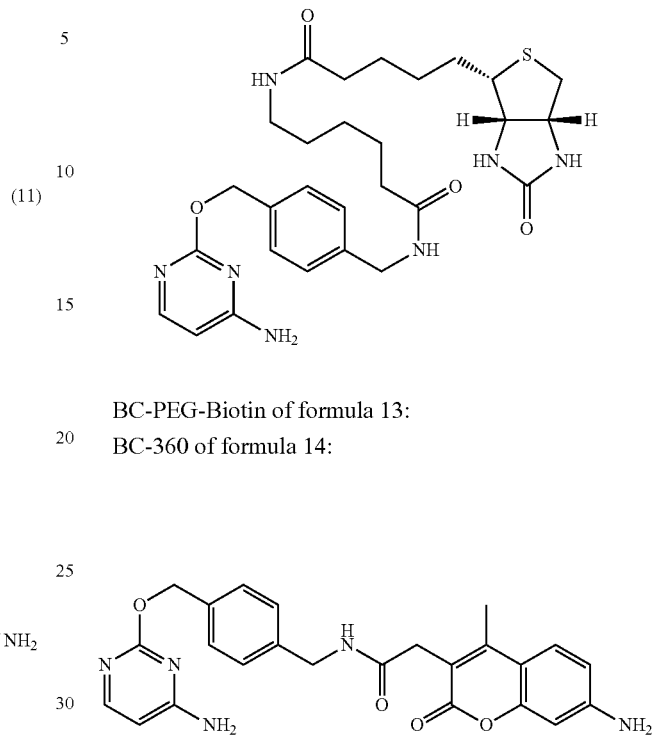

BC-PEG-Biotin of formula 13:
BC-360 of formula 14:

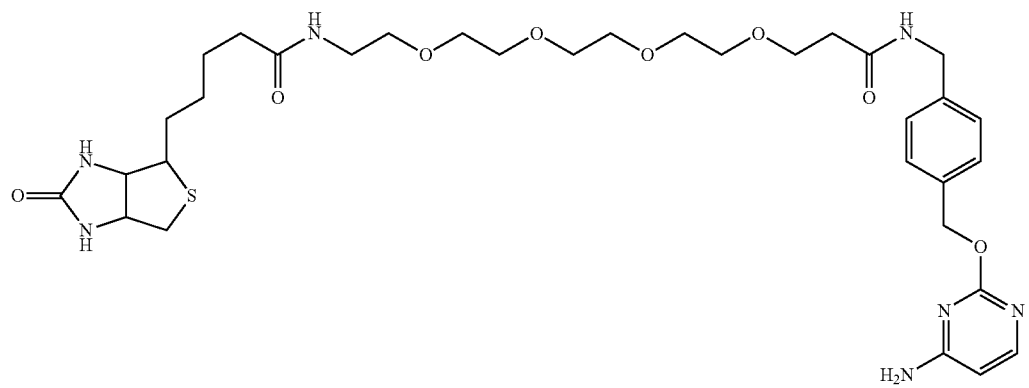

BC-430 of formula 15:

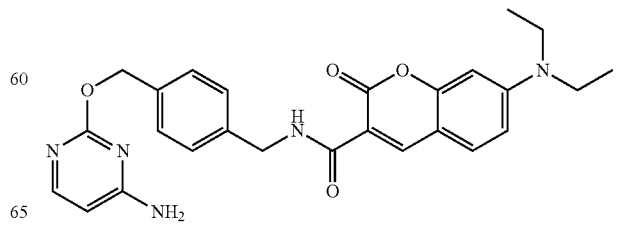

BC-Oregon Green consisting of a mixture of compounds of formula 16:

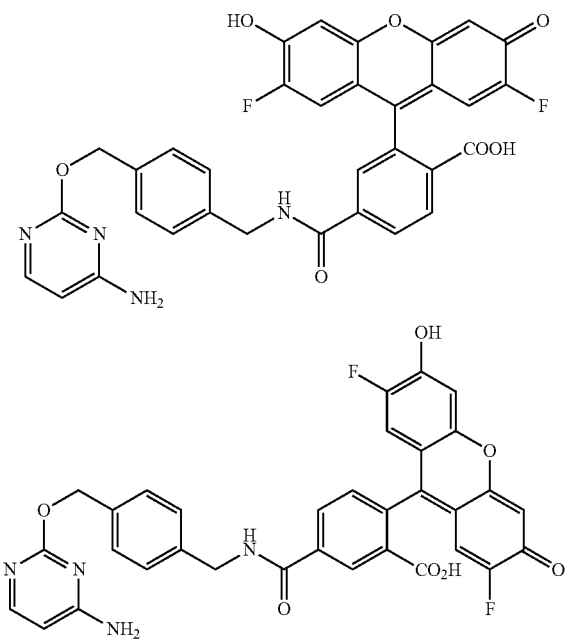

BC-Oregon Green dipivaloyl ester consisting of a mixture of compounds of formula 17:

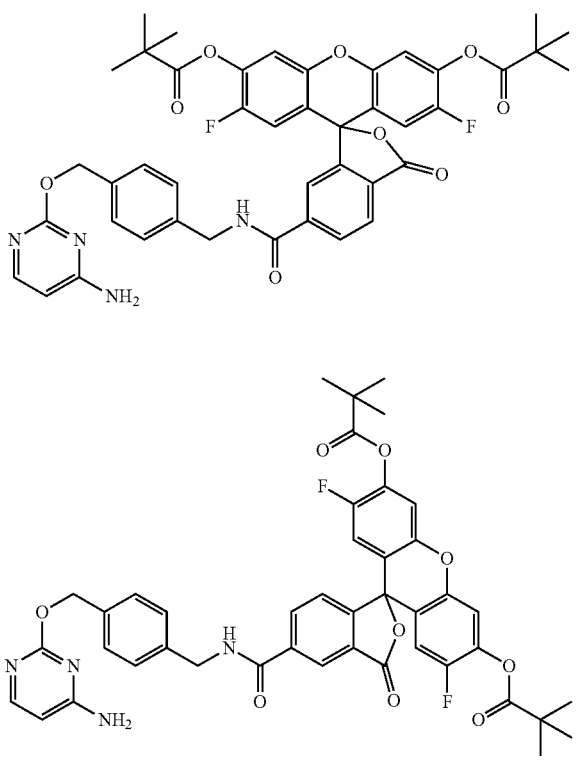

BC-505 consisting of a mixture of compounds of formula 18:

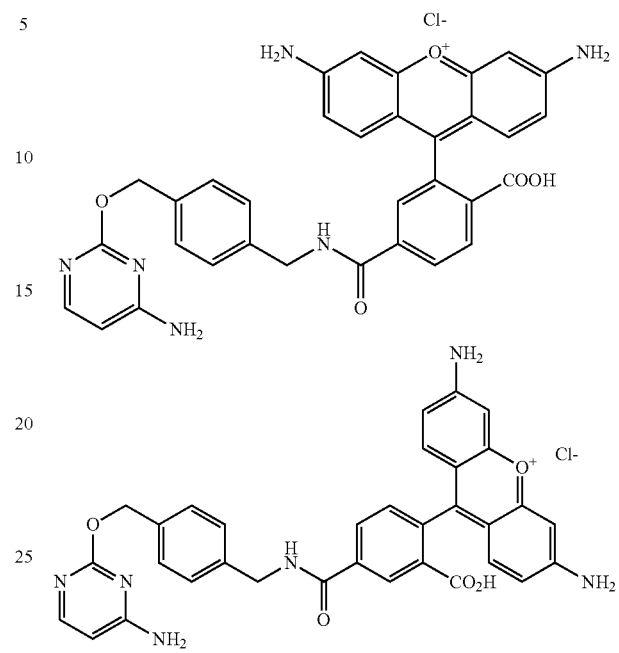

Example 11

Library Construction and Phage Selection

Overlap extension PCR using primers 1-5 and $^{N}$AGT gene (SEQ ID NO:2) as template allowed to randomize the residues 114, 131, 135, 148, 156, 157 and 159 of $^{N}$AGT. $^{N}$AGT is a 182 amino acid mutant of $^{wt}$AGT in which the last 25 amino acids are deleted and that possesses the mutations K32I, L33F, C62A, Q115S, Q116H, K125A, A127T, R128A, G131K, G132T, M134L, R135S, N150Q, 1151G, N152D, G153L, A154D, N157G and S159E (Gronemeyer et al., Protein Eng. Des. Set. 19:309-316, 2006). Primers 1 (N, AGT, SEQ ID NO:3) and 2 (C, AGT, SEQ ID NO:4) contain Sfi1 restriction sites; Primer 3 (SEQ ID NO:5) contains the randomized bases for randomization at position 114; Primer 4 (SEQ ID NO:6) contains the randomized bases for randomization at position 131 and 135; Primer 5 (SEQ ID NO:7) contains the randomized bases for randomization at position 148, 156, 157 and 159. The PCR product was ligated into phage display vector pAK100 and the resulting construct was electroporated into E. coli XL1-blue (Stratagene, USA). This led to a library containing about $10^7$ clones.

Library cells were grown in 2YT medium (25 µg/mL chloramphenicol, 1% glucose, 1 mM $MgCl_2$) at 37° C. until the optical density $OD_{600}$ reached 0.6. Then $2\times10^{10}$ VCS M13 helper phages were added and the culture was incubated 30 min at 37° C. without shaking and 3 h at 37° C. at 170 rpm. Cells were harvested by centrifugation (4000 rpm, 5 min, RT), resuspended in SB-MOPS (50 mM 3-morpholinopropansulfonic acid, 25 µg/mL chlor-amphenicol, 70 µg/mL kanamycin, 1 mM $MgCl_2$) and incubated 1-4 h at 37° C. at 220 rpm, then overnight at 24° C. at 220 rpm. Cells were pelleted and the supernatant containing phages adjusted to 1 mM DTT and stored at 4° C. prior to selections. For selection, BCFL (compound 5) was added to the phage solution (1 mL)

to a final concentration of 5 µM, gently rotated for 30 min at room temperature. The reaction was quenched by addition of 8 µM BC and 200 µM BG. Phages were precipitated at 4° C. using polyethylene glycol 8000 (4% w/v) and NaCl (3% w/v), centrifuged in a desktop centrifuge (13000 rpm, 4° C.) and resuspended in 500 µL PBS. To this solution, 500 µL of PBSMM (PBS with 4% skimmed milk powder) were added and the solution was gently rotated for 60 min at room temperature. 200 µL of magnetic beads covered with anti-fluorescein antibody (washed twice with PBS and blocked for 60 min with PBSMM) were added to the phage preparation and rotated at 4° C. for 30 min. After immobilization of labelled phages, the beads were washed 3 times with PBSMM, 5 times with PBST (PBS with 0.05% Tween-20), twice with PBS. Phages were eluted by incubation of the beads with 100 µL 0.1 M glycine, pH 2.5 for 5 min and the solution was neutralized with 50 µL 1 M Tris-HCl pH 8. E. coli JM101 were infected with eluted phages, plated on 2YT plates supplemented with 1% glucose and 25 µg/mL chloramphenicol, then incubated overnight at 37° C. The next day, colonies were scraped off the plates, aliquoted and stored at −80° C. prior to the next round of selection. Six rounds of selection were performed.

Example 12

Characterization of Selected ACTs as GST Fusion Proteins

The genes of mutants isolated after phage selection according to Example 9 were amplified by PCR using primers 6 (N, AGT, SEQ ID NO:8) and 7 (C, AGT, SEQ ID NO:9) that contain, respectively, BamH1 and EcoR1 restriction sites for subsequent subcloning into pGEX-2T vector (Amersham Biosciences, Otelfingen, Switzerland). Expression and purification of proteins as GST-ACT fusion proteins were performed as previously described for AGT fusion proteins (A. Juillerat, T. Gronemeyer, A. Keppler, S. Grendreizig, H. Pick, H. Vogel, K. Johnsson, Chem. Biol. 10:313, 2003). Reaction rates of labelling with BCFL (compound 5) and BG carrying fluorescein (BGFL, WO 02/08397) were determined by incubation of corresponding ACT protein (0.2-0.4 µM) with the appropriate fluorogenic substrate (2-20 µM) in reaction buffer (50 mM HEPES, pH 7.2, 1 mM DTT, 200 µg/mL of BSA) at 24° C. Samples were taken at different times and the labelling reaction was quenched by addition of 4×SDS buffer (8% SDS, 10% β-mercaptoethanol, 240 mM Tris pH 6.8, 40% glycerol) and incubation at 95° C. for 5 min. The reaction advancement was determined by detection of the fluorescent dye-labelled proteins in SDS-PAGE gel and quantification of fluorescence intensity using a Pharox FX™ molecular imager. The data were fitted to a pseudo-first order reaction model.

Second-order rate constants were then obtained by dividing the pseudo first-order constant by the concentration of fluorogenic substrate.

Example 13

In Vitro Specific Dual Labelling Assays

In vitro dual labelling assays were performed by incubating an equimolar mixture of GST-ACT1 and 6×His-$^N$AGT (0.5 µM final concentration) with either BGFL (benzyl-guanine carrying fluorescein, WO 02/08397), BGCy5 (benzylguanine carrying fluorescent dye Cy5, compound 11, Example 9), BCFL (compound 5, Example 4), BCCy5 (compound 10, Example 8) (5 µM) or an equimolar mixture of BGCy5/BCFL or BGFL/BCCy5 (5 µM each) in reaction buffer (50 mM HEPES, pH 7.2, 1 mM DTT, 200 µg/mL of BSA) at 24° C. for 60 minutes. Labelling reactions were quenched by addition of 4×SDS buffer (8% SDS, 10% β-mercaptoethanol, 240 mM Tris pH 6.8, 40% glycerol) and incubation for 5 min at 95° C. Fluorescent dye-labelled protein mixtures were analyzed by SDS-PAGE as described above.

Example 14

Construction of Mammalian Cell Expression Vector

For expression of fusion proteins $^N$AGT-NLS3, $^N$AGT-βGal, ACT1-NLS3 and ACT1 βGal in mammalian cells, $^N$AGT and ACT1 genes were PCR amplified using primers 8 (N, AGT, SEQ ID NO:10) and 9 (C, AGT, SEQ ID NO:11) and inserted into NheI/BglII restriction sites of the mammalian expression vector pECFP-Nuc (Clontech) or a mammalian expression plasmid containing the β-galactosidase gene.

The invention claimed is:

1. A compound of formula (I)

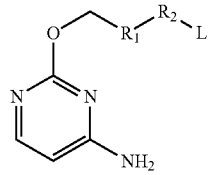

(I)

wherein $R_1$ is an aromatic or a heteroaromatic group, or an optionally substituted unsaturated alkyl, cycloalkyl or heterocyclyl group with a double bond connected to $OCH_2$—;

$R_2$ is a linker; and

L is a label or a plurality of same or different labels wherein L is a spectroscopic probe, a molecule representing one part of a specific binding pair, or a molecule covalently attached to a solid support.

2. The compound of formula (I) according to claim 1 wherein $R_1$ is phenyl.

3. The compound of formula (I) according to claim 2 wherein $R_1$ is para-substituted phenyl.

4. The compound of formula (I) according to claim 1 wherein $R_2$ is a straight or branched chain alkylene group with 1 to 300 carbon atoms, wherein optionally (a) one or more carbon atoms are replaced by oxygen, or every third carbon atom is replaced by oxygen, or one or more carbons is replaced by a poylethyleneoxy group with 1 to 100 ethyleneoxy units;

(b) one or more carbon atoms are replaced by nitrogen carrying a hydrogen atom, and the adjacent carbon atoms are substituted by oxo, representing an amide function —NH—CO—;

(c) one or more carbon atoms are replaced by oxygen, and the adjacent carbon atoms are substituted by oxo, representing an ester function —O—CO—;

(d) the bond between two adjacent carbon atoms is a double or a triple bond, representing a function —CH=CH— or —C≡C—;

(e) one or more carbon atoms are replaced by a phenylene, a saturated or unsaturated cycloalkylene, a saturated or unsaturated bicycloalkylene, a bridging heteroaromatic or a bridging saturated or unsaturated heterocyclyl group;

(f) two adjacent carbon atoms are replaced by a disulfide linkage —S—S—.

5. The compound of formula (I) according to claim 4 wherein $R_2$ is a straight chain alkylene group with 1 to 25 carbon atoms wherein carbon atoms are optionally replaced by an amide function —NH—CO—.

6. The compound of formula (I) according to claim 1 wherein L is a fluorophore.

7. The compound N-[4-(4-aminopyrimidin-2-yloxymethyl)-benzyl]-tetramethylrhodamine-5- or 6-carboxamide according to claim 6, or a mixture thereof.

8. The compound N-[4-(4-aminopyrimidin-2-yloxymethyl)-benzyl]-fluorescein-5 or 6-carboxamide according to claim 6, or a mixture thereof.

9. The compound N-[4-(4-aminopyrimidin-2-yloxymethyl)-benzyl]-diacetylfluorescein-5 or 6-carboxamide according to claim 6, or a mixture thereof.

10. The compound according to claim 6, N-[4-(4-aminopyrimidin-2-yloxymethyl)-benzyl]-DY647-carboxamide of formula 8:

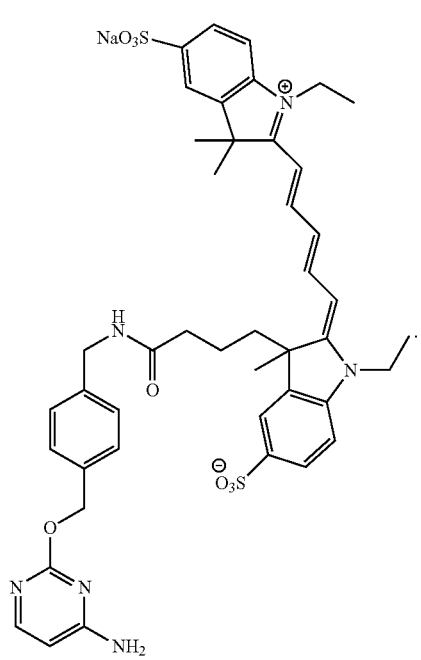

(8)

11. The compound according to claim 6, N-[4-(4-aminopyrimidin-2-yloxymethyl)-benzyl]-DY547-carboxamide of formula 9:

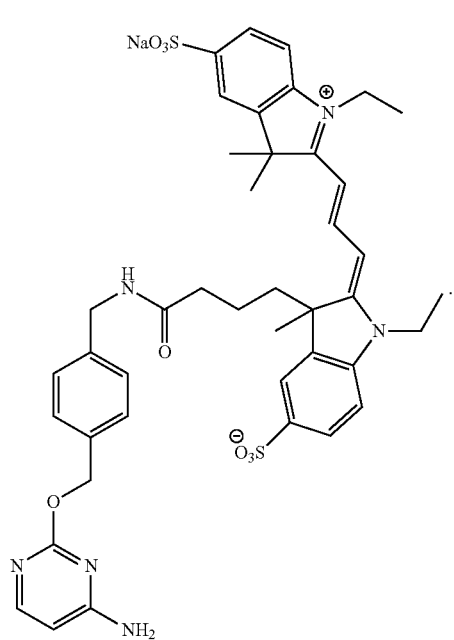

(9)

12. The compound according to claim 6, N-[4-(4-aminopyrimidin-2-yloxymethyl)-benzyl]-Cy5-carboxamide of formula 10:

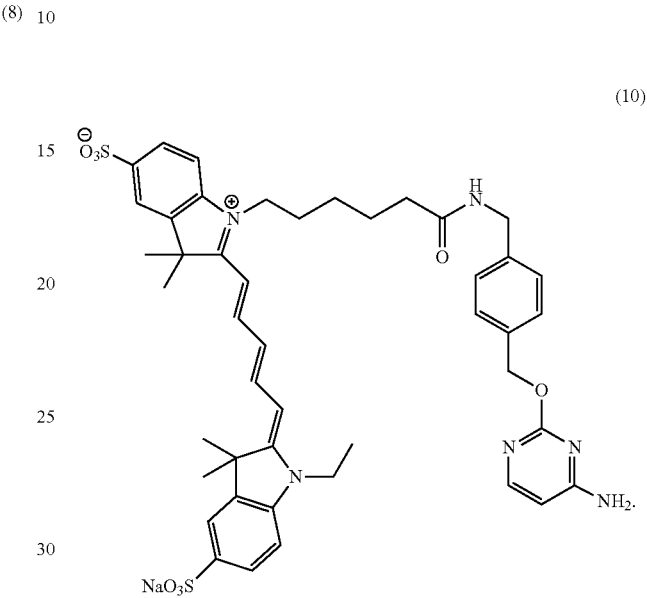

(10)

13. The compound BC-Biotin according to claim 6 of formula 12:

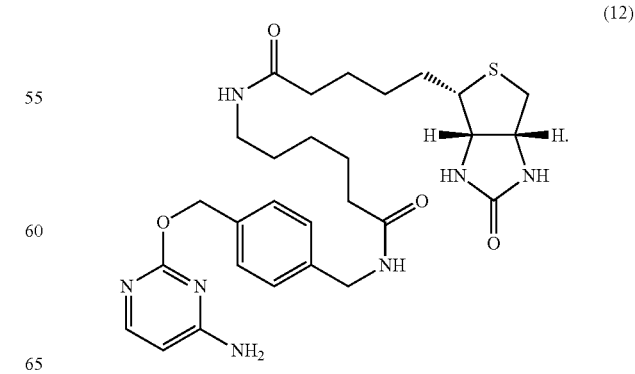

(12)

14. The compound BC-PEG-Biotin according to claim 6 of formula 13:
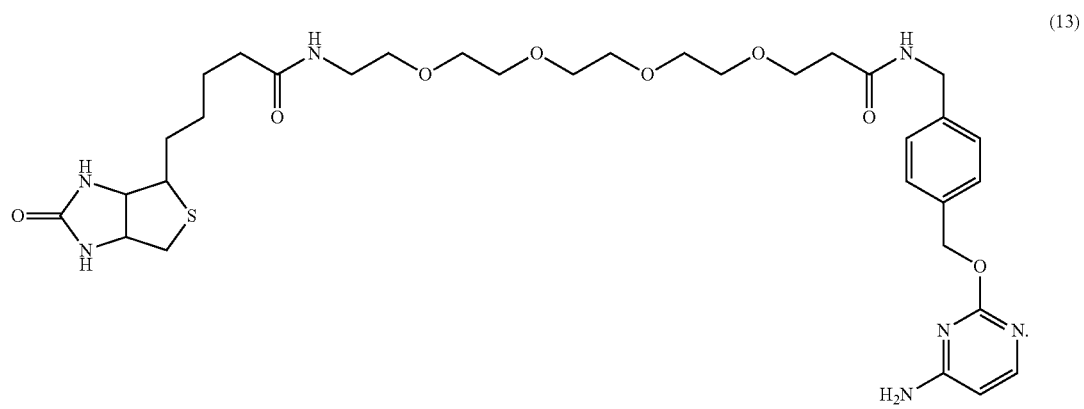
(13)
15. The compound BC-360 according to claim 6 of formula 14:
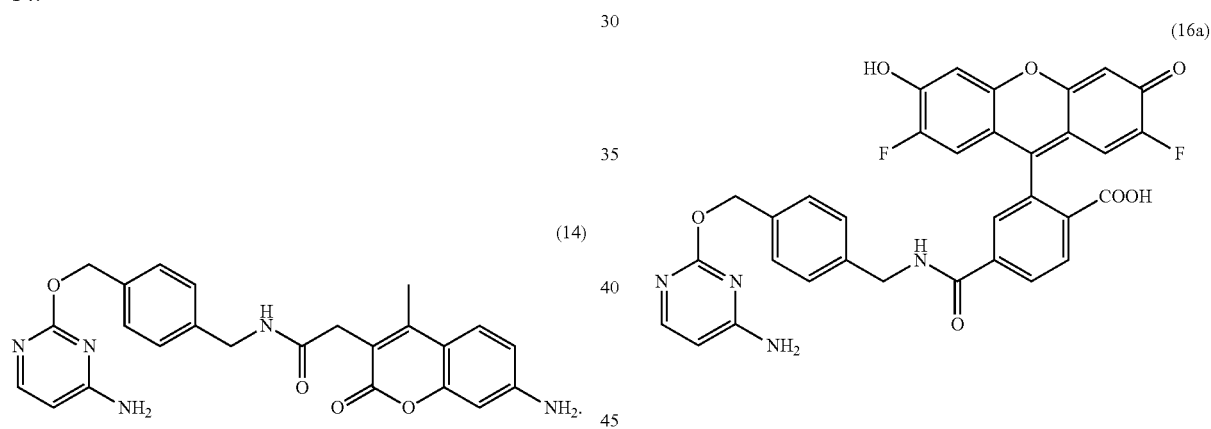
(14)
16. The compound BC-430 according to claim 6 of formula 15:
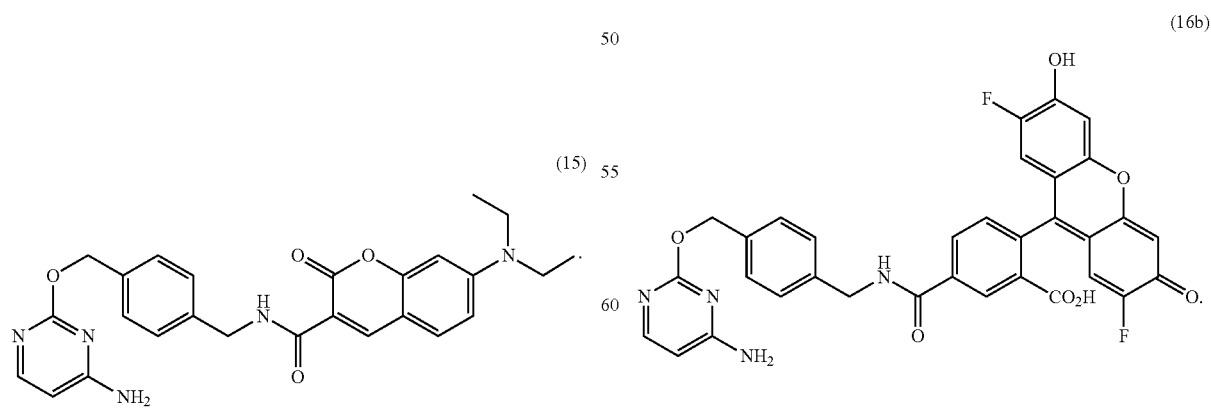
(15)
17. The compound BC-Oregon Green according to claim 6 of one of the formulas 16a or 16b or a mixture thereof:
(16a)
(16b)
18. The compound BC-Oregon Green dipivaloyl ester according to claim 6 of one of the formulas 17a or 17b or a mixture thereof:

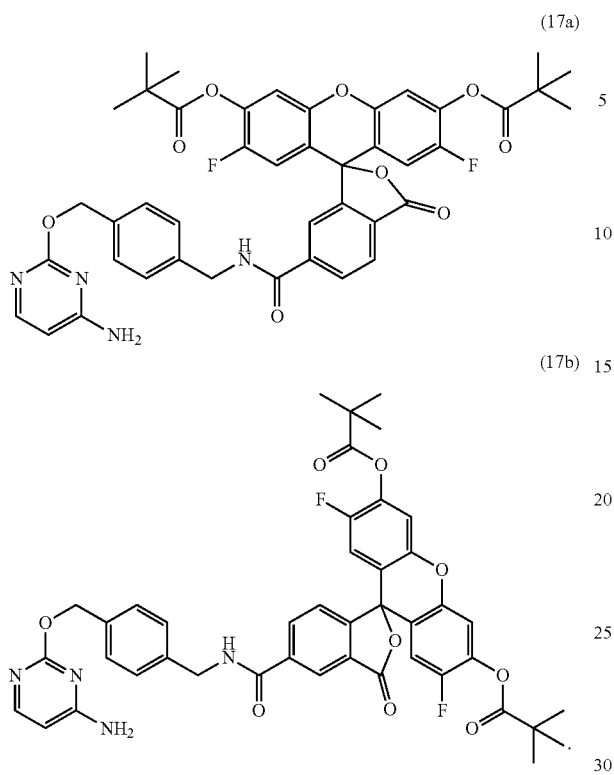
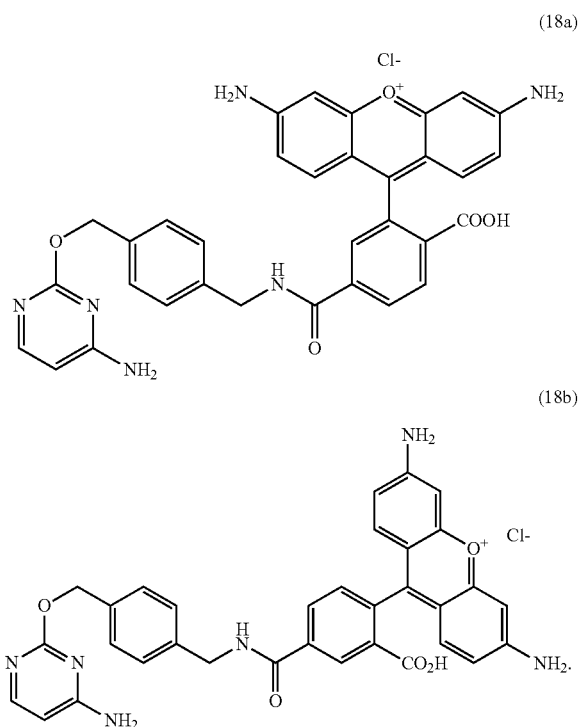
19. The compound BC-505 according to claim 6 of one of the formulas 18a or 18b or a mixture thereof:
* * * * *